United States Patent [19]
Pande et al.

[11] Patent Number: 6,133,433
[45] Date of Patent: Oct. 17, 2000

[54] METHOD FOR DETECTION AND PREVENTION OF HUMAN CYTOMEGALOVIRUS INFECTION

[75] Inventors: Hema Pande, Arcadia; Arthur D. Riggs, LaVerne; John A. Zaia, Arcadia; Brian R. Clark, Redwood City, all of Calif.

[73] Assignee: City of Hope, Duarte, Calif.

[21] Appl. No.: 08/469,920

[22] Filed: Jun. 6, 1995

Related U.S. Application Data

[63] Continuation-in-part of application No. 07/978,151, Nov. 17, 1992, abandoned, which is a continuation of application No. 07/307,526, Feb. 8, 1989, abandoned, which is a division of application No. 06/885,386, Jul. 16, 1986, Pat. No. 5,075,213, and a continuation of application No. 06/635,368, Jul. 27, 1984, abandoned.

[51] Int. Cl.[7] .......................... C07H 19/00; C07H 21/04; C07K 1/00; A61K 39/00
[52] U.S. Cl. .................... 536/22.1; 536/23.1; 536/23.72; 536/24.5; 530/403; 424/186.1; 424/184.1; 424/204.1; 435/69.1; 435/69.3; 435/71.2; 435/71.1; 435/91.1; 435/172.1
[58] Field of Search ............................... 435/320.1, 69.1, 435/69.3, 71.2, 71.1, 91.1, 172.1; 530/333, 350, 395, 403, 413, 416, 417; 424/186.1, 204.1, 230.1, 93.2, 184.1; 536/22.1, 23.1, 23.72, 24.5

[56] References Cited

U.S. PATENT DOCUMENTS

| | | | |
|---|---|---|---|
| 3,959,466 | 5/1976 | Plotkin | 424/89 |
| 4,058,598 | 11/1977 | Stern et al. | 424/89 |
| 4,289,690 | 9/1981 | Pestka | 530/351 |
| 4,358,535 | 11/1982 | Falkow et al. | 435/5 |
| 4,689,225 | 8/1987 | Pereira | 424/89 |
| 4,716,104 | 12/1987 | Harris et al. | 435/5 |
| 4,762,780 | 8/1988 | Spector et al. | 935/6 |
| 5,180,813 | 1/1993 | Stinski | 530/388.3 |
| 5,248,768 | 9/1993 | Lussenhop et al. | 530/395 |

OTHER PUBLICATIONS

Montgomery et al. "Heterologous an dhomologous protection against influenza a by DNA vaccination: Optimization of DNA vectors". DNA and Cell Biology. vol. 12, No. 9, pp. 777–783, 1993.

Forman et al. "A 64,000 dalton matrix protein of human cytomegalovirus induces in vitro immune responses similar to those of whole viral antigen". Journal of Immunology. vol. 134, No. 5, pp. 3391–3395/, May. 1985.

Plotkin et al. "Vaccines for the prevention of Human Cytomegalovirus Infection". Reviews of Infectious Diseases. vol. 12, Suppl. 7, pp. S827–S838, Sep. 1990.

Gibson et al. "selection of Particles for the use as Human Cytomegalovirus Subunit Vaccines." Birth defects Original articles Series: CMV: pathogenesis and prevention of human infection. Plotkin et al, Eds., vol. 20, No. 1, pp. 305–324, 1984.

Pachl et al. "The Human Cytomegalovirus Strain Towne Glycoprotein H Gene Encodes Glycoprotein p86." Virology. vol. 169, pp. 418–426, 1989.

Spaete et al. "Human Cytomegalovirus Strain Towne Glycoprotein B is Processed by Proteolytic Cleavage". Virology. vol. 167, pp. 207–225, 1988.

Smith, H. "Regulatory considerations for nucleic acid vaccines". Vaccine, vol. 12, No. 16, pp. 1515–1519, 1994.

Ellis, R. "New Technologies for making Vaccines". Vaccines, Chapter 29, Plotkin et al, Eds., W.B. Saunders Company, pp. 568–575, 1988.

Ruger et al. "Primary Structure and Transcription of the Genes Coding for Two Virion Phosphoproteins pp65 and pp71 of Human Cytomegalovirus". Journal of Virology, vol. 61, No. 2, pp. 446–453, Feb. 1987.

Pereira et al. "Monoclonal Antibodies to Human Cytomegalovirus: Three Surface Membrane Proteins with Unique Immunological and Electrophoretic Properties Specify Croos Reactive Determinants". Infection and Immunity. vol. 36, No. 3, pp. 924–932, Jun. 1982.

Clark et al. "Isolation and partial Chemical Charaterization of a 64,000–dalton Glycoprotein of Human Cytomegalovirus". Journal of Virology. vol. 49, No. 1, pp. 279–282, Jan. 1984.

Forman, et al., *J. Immunology* 134(5):3391–3395 (1985).
Clark et al. (1984) *J. Virol.* 49(1):279–282.
Mole et al. (1982) *Mol. Immunol.* 19, 1–11.
Tamashiro, J.C. et al., *J. Virology*, vol. 42, No. 2, 1982, pp. 547–557.
Nowak, B. et al. *Virology*, 134 (Apr. 1984): 91–102.
Ruger, B. et al., J. Virology 61 (Feb. 1987): 446–53.
Irmiere, A. et al., *Virology*, 130 (Oct. 1983): 118–133.
Pande, H., et al., *Proc. Nat'l. Acad. Sci.*, USA, vol. 81, No. 15, 1984 pp. 4965–4969.
Spector, S.A., *The Lancet*, Feb. 19, 1983, pp. 378–380.
Borysiewicz, L.K. et al. Human cytomegalovirus–specific cytotoxic T lymphocytes: requirements for in generation and specificity. Euro. J. Immunol., 13:804–809, 1983.

Pande, H. et al. Direct DNA Immunization of Mice with Plasmid DNA Encoding the Tegument Protein pp65 (ppUL83) of Human Cytomegalovirus Induces High Levels of Circulating Antibody to the Encoded Protein. Scand. J. Infect Dis. Suppl. 99:117–120, 1995.

(List continued on next page.)

*Primary Examiner*—Avis M. Davenport
*Attorney, Agent, or Firm*—Rothwell, Figg, Ernst & Kurz

[57] ABSTRACT

A DNA probe has been isolated which is capable of hybridizing to an oligonucleotide sequence coding for a polypeptide from a major 64 Kilodalton protein of human cytomegalovirus (HCMVgp64). The probe has a sequence of at least seventeen (17) to as many as seven hundred twenty-one (721) nucleotides. The DNA fragments coding for the major late protein of human cytomegalovirus (HCMVgp64) may be hybridized to DNA fragments of HCMV DNA from an individual having human cytomegalovirus infection. The major late protein of human cytomegalovirus (HCMVgp64) also reacts with T-lymphocytes of an individual after natural infection of that individual with human cytomegalovirus. Thus, the HCMVgp64 protein may be used as a vaccine to prevent HCMV infection.

8 Claims, 7 Drawing Sheets

OTHER PUBLICATIONS

Stinski, M.F. et al. Organization and Expression of the Immediate Early Genes of Human Cytomegalovirus. J. Virol., pp. 1–14, Apr. 1983.

Gibson, W. Structural and Nonstructural Proteins of Strain Colburn Cytomegalovirus. Virology 111, 516–537, 1981.

Plotkin, S.A. et al. Protective Effects of Towne Cytomegalovirus Vaccine Against Low–Passage Cytomegalovirus Administered as a Challenge. J. Infect. Dis., vol. 159, No. 5, May 1989.

Gonczol, E. et al. Humoral Immune Response to Cytomegalovirus Towne Vaccine Strain and to Toledo Low–Passage Strain. J. Infect. Dis., vol. 159, No. 5, May 1989.

Rubenstein, E. et al. Immune Response Mechanisms. Scientific American Medicine, 9–16, 1989.

Pande, H. et al. Human Cytomegalovirus Strain Towne pp65 Gene: Nucleotide Sequence and Expression in *Escherichia coli*. Virol. 182, 220–228, 1991.

Pande, H. et al. Structural Analysis of a 64–kDa Major Structural Protein of Human Cytomegalovirus (Towne): Identification of a Phosphorylation Site and Comparison to pp65 of HCMV (AD169). Virol. 178, 6–14, 1990.

Pande, H. et al. Genomic Localization of the Gene Encoding a 32–kDa Capsid Protein of Human Cytomegalovirus. Virol. 167, 306–310, 1988.

Weiner, D. et al. Identification of a Primate Cytomegalovirus Group–Common Protein Antigen. Virol. 115, 182–191, 1981.

Roby, C. et al. Characterization of Phosphoproteins and Protein Kinase Activity of Virions, Noninfectious Enveloped Particles, and Dense Bodies of Human Cytomegalovirus. J. Virol., 714–727, Sep. 1986.

Churchill, M.A. et al. Quantitation of Human Cytomegalovirus DNA in Lungs from Bone Marrow Transplant Recipients with Interstitial Pneumonia. J. Infect. Dis., vol. 155, No. 3, Mar. 1987.

Del Valle, Ursino et al. Two–Column System for Determination of Glucosamine, Galactosamine, and Amino Acids on a Beckman 121MB Amino Acid Analyzer: Separation of the Anomers of Glucosamine and Galactosamine. Anal. Biochem. 96, 77–83, 1979.

Plotkin, S.A. et al. Effect of Towne Live Virus Vaccine on Cytomegalovirus Disease after Renal Transplant. Annals of Internal Medicine, vol. 114, No. 7, Apr. 1, 1991.

Roberts, M.R. et al. Targeting of Human Immunodeficiency Virus–Infected Cells by $CD8^-$ T Lymphocytes Armed With Universal T–Cell Receptors. Blood, vol. 84, No. 9, 2878–2889, Nov. 1, 1994.

Fleckenstein, B. et al. Cloning of the complete human cytomegalovirus genome in cosmids. Gene, 18, 39–46, 1982.

Gelmann, E.P. et al. Characterization and location of myc homologous sequences in human cytomegalovirus DNA. Proc. Natl. Acad. Sci. USA 80, 1983, 5107–5111.

FIG. 1
AMINO ACID SEQUENCE    Tyr-Gln-Glu-Phe-Phe-Trp-Asp
POSSIBLE CODONS    5' UA$^U_C$ CA$^A_G$ GA$^A_G$ UU$^U_C$ UU$^U_C$ UGG GA$^C_U$ 3'
HCMV PROBE 1    5'    CA$^A_G$ GA$^A_G$ TT$^T_C$ TT$^T_C$ TGG GA 3'
HCMV PROBE 2    5'    TA$^T_C$ CA$^A_G$ GA$^A_G$ TT$^T_C$ TT$^T_C$ TGG GA 3'
FIG. 3
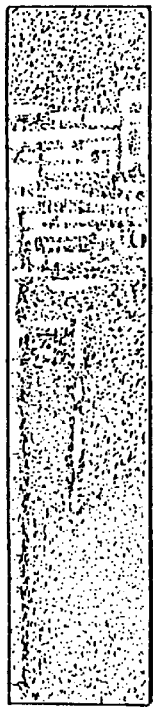
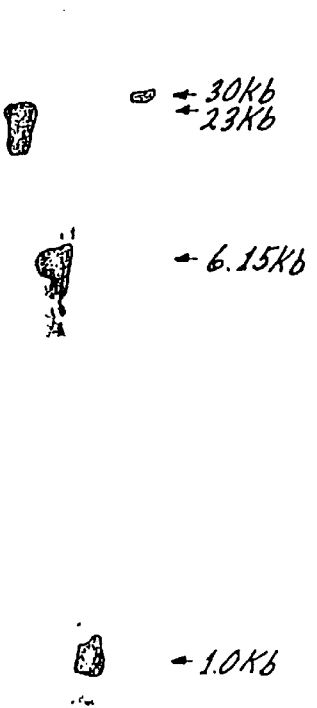
← 30Kb
← 23Kb
← 6.15Kb
← 1.0Kb

FIG. 2

```
Asn Leu Val Pro Met Val Ala Thr Val Gln Gly Gln Asn
AAC CTG GTG CCC ATG GTG GCT ACG GTT CAG GGT CAG AAT
                                         └─── T-14 ───┘

┌Tyr Gln Glu Phe Phe Trp Asp Ala Asn Asp Ile
     │TAC CAG GAG TTC TTC TGG GAC GCC AAC GAC ATC
Leu Lys                                    └─── T-12 ───┘
CTG AAG

┌Ile Phe Ala Glu Leu Glu Gly Val Trp Gln
     │ATC TTC GCC GAA TTG GAA GGG GTA TGG CAG
Tyr Arg
TAC CGT

┌Pro Ala Ala Gln Pro Lys
     │CCC GCT GCG CAA CCC AAA
Pro
CCC
```

FIG. 5

NUCLEOTIDE SEQUENCE OF HCMVgp64 GENE FRAGMENT

```
  1   GAT  CGG  ACT  CCG  ACG  AGG  AAC  TCG  TAA  CCA   30
 31   CCG  AGC  GCA  AGA  CGC  CCC  GCG  TTA  CCG  GCG   60
 61   GCG  GCG  CAT  GGC  GGG  CGT  CCA  CTT  CCG  CGG   90
 91   GCC  GCA  AAC  GCA  AAT  CAG  CAT  CCT  CGG  CGA  120
121   CGG  CGT  GCA  CGG  CGG  GCG  TTA  TGA  CAC  GCG  150
151   GCC  GCC  TTA  AGG  CCG  AGT  CCA  CCG  TCG  CGC  180
181   CCG  AAG  AGG  ACA  CCG  ACG  AGG  ATT  CCG  ACA  210
211   ACG  AAA  TCC  ACA  ATC  CGG  CCG  TGT  TCA  CCT  240
241   GGC  CGC  CCT  GGC  AGG  CCG  GCA  TCC  TGG  CCC  270
271   GCA  ACC  TGG  TGC  CCA  TGG  TGG  CTA  CGG  TTC  300
301   AGG  GTC  AGA  ATC  TGA  AGT  ACC  AGG  AGT  TCT  330
331   TCT  GGG  ACG  CCA  ACG  ACA  TCT  ACC  GCA  TCT  360
361   TCG  CCG  AAT  TGG  AAG  GCG  TAT  GGC  AGC  CCG  390
391   CTG  CGC  AAC  CCA  AAC  GTC  GCC  GCC  ACC  GGC  420
421   AAG  ACG  CCT  TGC  CCG  GGC  CAT  GCA  TTC  GCC  450
451   TCG  ACG  CCC  AAA  AAG  CAC  CGA  GGT  TGA  GCC  480
481   ACC  CGC  CGC  GCA  CGC  TTA  GGA  CGA  CTC  TAT  510
511   AAA  AAC  CCA  CGT  CCA  CTC  AGA  CAC  GCG  ACT  540
541   TTT  GGC  CGC  CAC  ACC  TGT  CGC  CGC  TGC  TAT  570
571   ATT  TGC  GAC  AGT  TGC  CGG  AAC  CCT  TCC  CGA  600
601   CCT  CCC  ACG  AAG  ACC  CGT  TCA  CCT  TTG  CGC  630
631   ATC  CCC  TGA  CCC  CCC  CCC  TCA  TCC  CGC  CTT  660
661   CGC  GAT  GTC  TCA  GGC  ATC  GTC  CTC  GCC  CGG  690
691   TGA  GGG  ACC  CTC  GTC  GGA  AGC  GGC  CGC  GAT  720
721   C                                                  721
```

FIG. 6

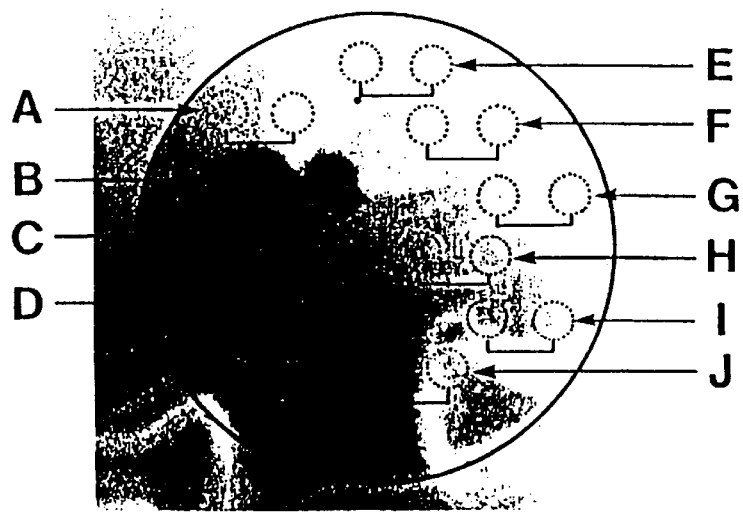

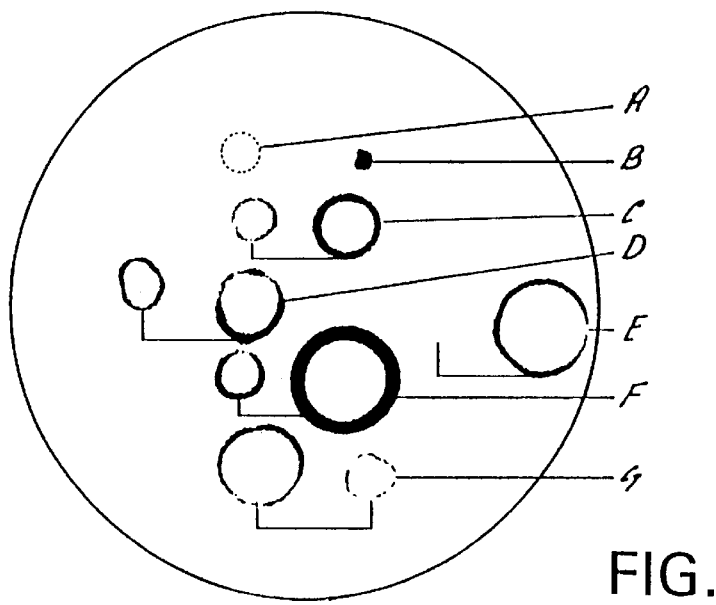

FIG. 7

DOT BLOT ANALYSIS OF WILD ISOLATES. ANALYSIS WAS PERFORMED USING INFECTED CELL LYSATE FROM WILD ISOLATES UNDER THE CONDITIONS DESCRIBED IN FIG. 7. THE AUTORADIOGRAM SHOWS HYBRIDIZATION OF $^{32}$P-LABELED CLONED HCMV-gp64 GENE FRAGMENT TO ALL THE WILD ISOLATES.

A - UNINFECTED CELLS (CONTROL)
B - HCMV (TOWNE)
C, E & G - GRANULOCYTE CULTURE OF PATIENTS AFTER BONE MARROW TRANSPLANTATION
D - LUNG CULTURE OF A PATIENT WITH HCMV ASSOCIATED PNEUMONIA
F - GRANULOCYTA CULTURE OF A PATIENT WITH ACUTE IMMUNODEFICIENCY SYNDROME (AIDS)

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

CARGARTTYT TYTGGGAY                                              18

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:2:

TAYCARGART TYTTYTGGGA Y                                     21

(2) INFORMATION FOR SEQ ID NO:3:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:3:

Tyr Gln Glu Phe Phe Trp Asp
1               5

(2) INFORMATION FOR SEQ ID NO:4:

(i) SEQUENCE CHARACTERISTICS:
      (A) LENGTH: 132 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:4:

AACCTGGTGC CCATGGTGGC TACGGTTCAG GGTCAGAATC TGAAGTACCA GGAGTTCTTC    60

TGGGACGCCA ACGACATCTA CCGCATCTTC GCCGAATTGG AAGGCGTATG GCAGCCCGCT  120

GCGCAACCCA AA                                                              132

(2) INFORMATION FOR SEQ ID NO:5:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Asn Leu Val Pro Met Val Ala Thr Val Gln Gly Gln Asn Leu Lys Tyr
 1               5                  10                  15

Gln Glu Phe Phe Trp Asp Ala Asn Asp Ile Tyr Arg Ile Phe Ala Glu
            20                  25                  30

Leu Glu Gly Val Trp Gln Pro Ala Ala Gln Pro
        35                  40

(2) INFORMATION FOR SEQ ID NO:6:

(i) SEQUENCE CHARACTERISTICS:
        (A) LENGTH: 721 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

GATCGGACTC CGACGAGGAA CTCGTAACCA CCGAGCGCAA GACGCCCCGC GTTACCGGCG      60

GCGGCGCATG GCGGGCGTCC ACTTCCGCGG GCGGCAAAGG CAAATCAGCA TCCTCGGCGA     120

CGGCGTGCAC GGCGGGCGTT ATGACACGCG GCCGCCTTAA GGCCGAGTCC ACCGTCGCGC     180

CCGAAGAGGA CACCGACGAG GATTCCGACA ACGAAATCCA CAATCCGGCC GTGTTCACCT     240

GGCCGCCCTG GCAGGCCGGC ATCCTGGCCC GCAACCTGGT GCCCATGGTG GCTACGGTTC     300

AGGGTCAGAA TCTGAAGTAC CAGGAGTTCT TCTGGGACGC CAACGACATC TACCGCATCT     360

TCGCCGAATT GGAAGGCGTA TGGCAGCCCG CTGCGCAACC CAAACGTCGC CGCCACCGGC     420

AAGACGCCTT GGCCGGGCCA TGCATTCGCC TCGACGCCCA AAAAGCACCG AGGTTGAGCC     480

ACCCGCCGCG CACGCTTAGG ACGACTCTAT AAAAACCCAC GTCCACTCAG ACACGCGACT     540

TTTGGCCGCC ACACCTGTCG CCGCTGCTAT ATTTGCGAGA GTTGCCGGAA CCCTTCCCGA     600

CCTCCCACGA AGACCCGTTC ACCTTTGCGC ATCCCCTGAC CCCCCCCCTC ATCCCGCCTT     660

CGCGATGTCT CAGGCATCGT GCTCGCCCGG TGAGGGACCC TCGTCGGAAG CGGCCGCGAT     720

C                                                                     721

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein -continued

```
    (xi) SEQUENCE DESCRIPTION: SEQ ID NO:7:

Gln Glu Phe Phe Trp Asp
1               5
```

METHOD FOR DETECTION AND PREVENTION OF HUMAN CYTOMEGALOVIRUS INFECTION

This application is a continuation-in-part of Ser. No. 07/978,151 filed Nov. 17, 1992 (abandoned), which is a continuation of Ser. No. 07/307,526 filed Feb. 8, 1989 (abandoned), which is a division of Ser. No. 06/885,386 filed Jul. 16, 1986 (issued as U.S. Pat. No. 5,075,213) and a continuation of Ser. NO. 06/635,368 filed Jul. 27, 1984 (abandoned).

This invention was made with Government support under Grant No. P01 CA 30206, awarded by the National Institutes of Health.

This invention relates to methods of diagnosing and preventing human cytomegalovirus infection. It also relates to probes used in diagnosing human cytomagalovirus and to medicines such as vaccines for preventing human cytomegalovirus.

Human cytomegalovirus is a member of the herpes virus group and is a relatively common form of disease. For example, approximately ten percent (10%) of all newborn infants carry human cytomegalovirus. Some of these newborn infants suffer congenital birth defects. Other newborn infants carry cytomegalovirus for some time before they actually show symptoms of the disease. People infected with the disease often suffer impairment of some of their vital organs, including the salivary glands, brain, kidney, liver and lungs, as a result of the effects of the disease. Furthermore, human cytomegalovirus is associated with a wide spectrum of classical syndromes including mononucleosis and interstitial pneumonia. Human cytomegalovirus also has an oncogenic potential and a possible association with certain types of malignancy including Karposi's sarcoma.

Since human cytomegalovirus is relatively common in people, a considerable effort has been made to isolate the disease and to diagnose the disease in patients. Attempts have also been made to prepare a medicine, such as a vaccine, which can be administered to a patient to prevent the disease. In spite of such efforts, no satisfactory method has been developed to isolate, diagnose or treat the disease.

This invention relates to methods of using DNA fragments coding for the major late 64 Kilodalton protein of human cytomegalovirus (HCMVgp64) to diagnose and prevent the disease. The invention also relates to probes formed from DNA fragments coding for this 64K protein of human cytomegalovirus for use in diagnosing cytomegalovirus in human patients. The invention also relates to vaccines formed from matrix proteins such as HCMVgp64 of human cytomegalovirus for use in preventing the disease. The probes and vaccines can be manufactured simply and reliably and can be applied by technicians to patients to obtain reliable results.

In one embodiment of the invention, a probe is capable of hybridizing to a gene fragment coding for an amino acid sequence of HCMVgp64 protein of human cytomegalovirus. The probe has a sequence of at least seventeen (17) to seven hundred twenty-one (721) nucleotides. The probe may be radioactivity labeled. The probe is used to screen DNA fragments constituting a subgenomic library of human cytomegalovirus DNA to obtain DNA fragments coding for the HCMVgp64 of human cytomegalovirus.

The DNA fragments coding for the HCMVgp64 of human cytomegalovirus may be hybridized to whole DNA or to DNA fragments of the DNA of an individual having human cytomegalovirus. The DNA fragments may be formed by digesting the human cytomegalovirus DNA with a restriction endonuclease such as one of the restriction endonucleases EcoRI, BamHI, XbaI, HindIII and PstI. During the "dot-blot" screening procedure, the DNA fragments coding for the HCMVgp64 protein of human cytomegalovirus hybridizes to the DNA of HCMV. As a result of such hybridization, the identity of human cytomegalovirus may be established. This particular DNA fragment may have a map location of approximately 0.50 to 0.51 units in the human cytomegalovirus genome. It may have a sequence of about seven hundred twenty-one (721) nucleotides.

The major late protein of human cytomegalovirus (HCMVgp64) also reacts with T-lymphocytes in an individual after natural infection of that individual with human cytomegalovirus. Thus, the HCMVgp64 protein may be used as a vaccine to treat patients having human cytomegalovirus.

In the drawings:

FIG. 1 is a schematic drawing illustrating the sequence of nucleotides in oligonucleotide probes (SEQ ID NOS: 1 and 2) used in isolating and characterizing a genomic clone containing the gene fragment coding for an amino acid sequence of a tryptic peptide of a matrix protein (SEQ ID NO: 3), such as a 64K dalton glycoprotein, which is the major late antigen of human cytomegalovirus;

FIG. 2 is a schematic drawing of the sequence of nucleotides (SEQ ID NO: 4)and the sequence of the amino acids (SEQ ID NO: 5)of a gene fragment coding for the matrix protein, such as a 64K glycoprotein, of human cytomegalovirus;

FIG. 3A is a representation of the DNA fragments obtained by digesting the cytomegalovirus DNA with different restriction endonucleases and transferring the DNA fragments to nitrocellulose;

Figure 4:
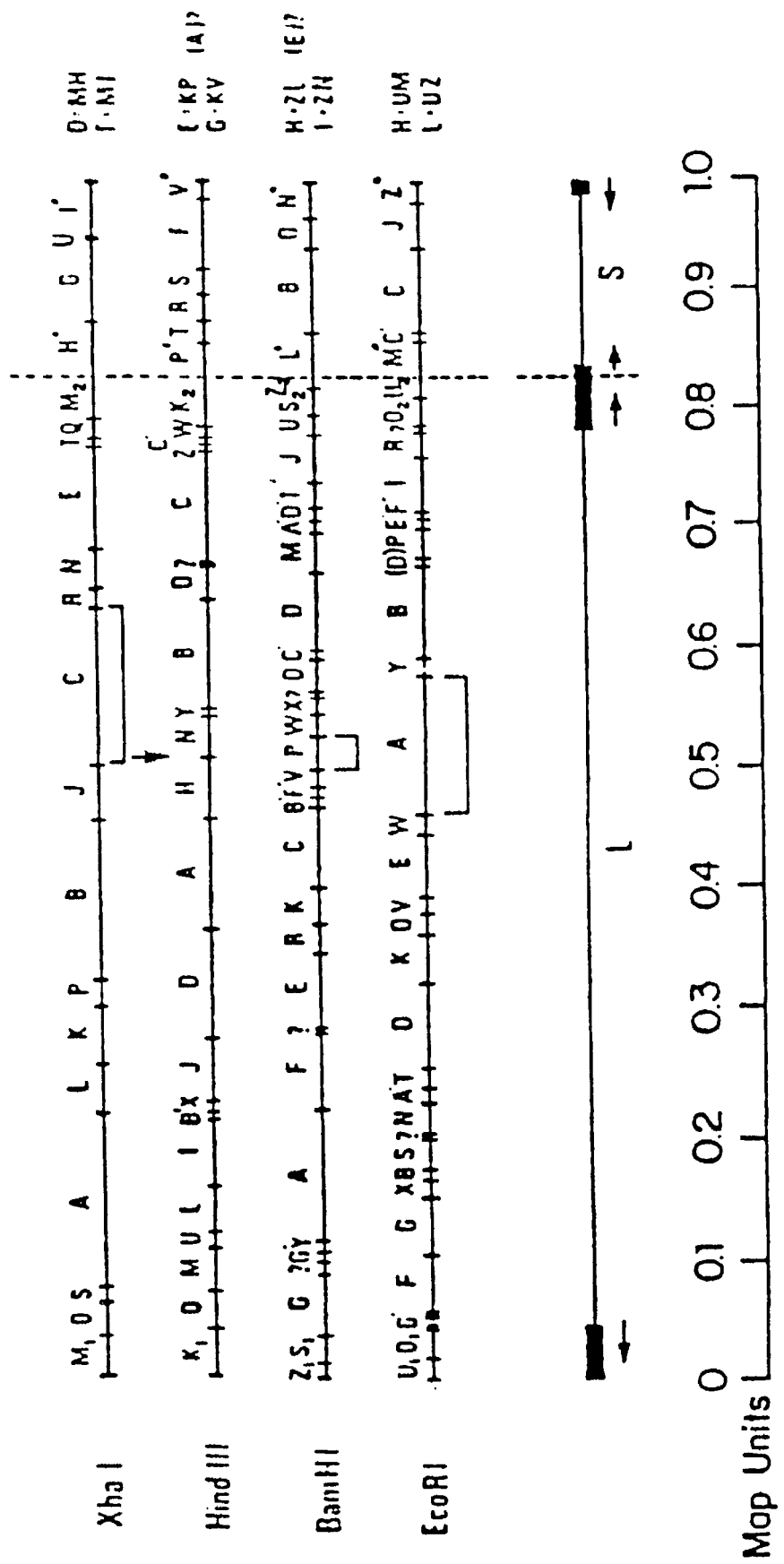

FIG. 3B is a representation of the results of hybridizing the DNA fragments of FIG. 3A with a labelled, purified and cloned DNA fragment having a sequence of seven hundred twenty-one (721) base pairs; and FIG. 4 is a representation of the mapping of the DNA fragments obtained by digesting the DNA of human cytomegalovirus with the different restriction endonucleases and particularly illustrates the relative location of a particular one of the DNA fragments obtained from such digestion.

FIG. 5 is a table indicating the nucleotide sequence found to exist for a particular gene fragment of human cytomegalovirus (SEQ ID NO: 6); and FIG. 6 is a dot-blot indicating the detection of human cytomegalovirus and the non-detection of other types of herpes viruses.

FIG. 7 is a dot blot indicating the detection of human cytomegalovirus from chemical specimens.

The human cytomegalovirus (HCMV) genome is a linear double-stranded molecule with an approximate size of 240 kilobase pair (kb). The cytomegalovirus DNA consists of a long region and a short region of unique nucleotide sequences which are bounded by inverted repeat regions. Human cytomegalovirus specifies more than 50 unique infected-cell polypeptides with molecular weights ranging from 200 to 10 kDa. Of these, a matrix protein of human cytomegalovirus, such as a major structural glycoprotein having an Mr (relative mass) of approximately 64–66 K dalton (HCMVgp64), is present in high abundance during the late stages of human cytomegalovirus infection and is an important antigenic component in serologic tests for human cytomegalovirus. An antibody to the matrix protein of human cytomegalovirus (HCMVgp64) appears after natural infection in both adults and children. HCMVgp64 constitutes a 64K dalton glycoprotein which is the major late synthesis of human cytomegalovirus. A monoclonal antibody specific for this viral protein neutralizes virus infectivity and binds to the plasma membrane of infected cells.

To further an understanding of the precise role of the matrix protein of human cytomegalovirus, such as the 64K dalton glycoprotein (HCMVgp64), in natural human cytomegalovirus infection, applicants attempted to clone the gene coding for this structural protein. Although this polypeptide has been purified from the virions plus dense bodies (HCMV-db) of HCMV, no one has previously identified the portion of the cytomegalovirus DNA coding for this protein.

This invention describes the cloning of a gene fragment coding for a matrix protein of human cytomegalovirus, such as the 64K dalton glycoprotein (HCMVgp64), by means of oligonucleotide probing. Since none of the structural polypeptides of HCMV have been previously mapped, a significant aspect of this invention is the physical mapping of the coding sequences of the matrix protein of human cytomegalovirus HCMVgp64. As will be seen, all of this is used to diagnose human cytomegalovirus in patients and to provide a vaccine for immunizing patients.

MATERIALS AND METHODS

Growth of HCMV. Human cytomegalovirus (HCMV) (Towne strain) was obtained from S. Starr, Philadelphia, Pa., and grown in human foreskin fibroblasts. The growth medium consisted of Dulbecco's modified Eagle medium, supplemented with 10% fetal bovine serum. This medium was maintained in a 10% $CO_2$/90% air atmosphere at 36° C. Fibroblast monolayer cultures were grown in 485 $cm^2$ roller bottles and inoculated with cell-free virus using a multiplicity of infection of 0.1–0.2. Extracellular virus was harvested and virions plus dense bodies (HCMV-db) were prepared as described by B. R. Clark, J. A. Zaia, L. Balce-Directo and Y. P. Ting in 1984 in 49 Journal of Virology 279–282.

Isolation, trypsin digestion and microsequence analysis of HCMVgp64. HCMVgp64 (the 64K dalton glycoprotein) was purified from HCMV-db by reverse phase high performance liquid chromatography as described in 1984 in an article in 49 Journal of Virology 279–282. (Although reference may be made in this application to HCMVgp64, it will be appreciated that this may be considered broadly to be a matrix protein of human cytomegalovirus). Trypsin digestion and separation of tryptic peptides were obtained as specified in 1984 in the article in 49 Journal of Virology 279–282. Amino acid analysis of tryptic peptides was performed on a Beckman 121 MB amino acid analyzer according to the procedures described by U. Del Valle and J. E. Shively in 1979 in 96 Analytical Biochemistry 77–83. Amino terminal sequence analysis of the tryptic peptides was performed by using microseauencing techniques by automated Edman degradation on a modified Beckman 890C sequencer by the method of Shively as described in 1981 in 79 Methods in Enzymology 31–48.

Synthesis of mixed oligodeoxynucleotides. Mixed oligonucleotides seventeen (17) bases and twenty (20) bases long were synthesized by a solid phase phosphotriester approach using protected dinucleotides as described by Z. K. Tan, F. Ikuta, T. liuang, A. Dugaiczk and K. Itakura in 1982 in 47 Cold Spring Harbor Symposium of Quantitative Biology at pages 387–391. The synthetic oligonucleotides seventeen (17) bases and twenty (20) bases long were provided with overlapping relationships as shown in FIG. 1 where the oligonucleotides are designated as HCMV probe 1 and HCMV probe 2. The nucleotide sequences of these probes were based upon the partial amino acid sequence of the matrix protein of human cytomegalovirus (designated in this application as HCMVgp64).

A heptapeptide sequence derived from a tryptic fragment of the matrix protein of human cytomegalovirus (HCMVgp64) was selected for the design of two (2) sets of oligonucleotide mixtures containing all of the possible coding sequences as shown in FIG. 1. Both probes were synthesized in one main synthesis. The first set (designated as HCMV probe 1) was derived from the hexapeptide sequence Gln-Glu-Phe-Phe-Trp-Asp (SEQ ID NO: 7) and was synthesized as a mixture of sixteen (16) different heptanucleotides. This mixture of sixteen (16) different oligonucleotides resulted from the variations possible in the third position of each amino acid codon, as may be seen in FIG. 1 from the two indications above each other in the third position for each amino acid sequence.

At the completion of the synthesis of HCMV probe 1, the resin was split and half of it was used for the synthesis of the second probe. The second probe (HCMV probe 2) was based on a heptapeptide sequence derived from the hexapeptide discussed above but containing an additional tyrosine at the $NH_2$ terminus as shown in FIG. 1. This second set of oligonucleotides was synthesized as a mixture of thirty-two (32) different icosanucleotides. It involved two (2) additional couplings to the second half of the resin.

The oligonucleotides were purified by high performance liquid chromatography on a reverse phase column (Waters Associates p-Bondapak C-18). Labeling of the purified oligodeoxynucleotides at the 5' end was performed by using T4 polynucleotide kinase and [$\gamma^{32P}$] ATP. The radioactively labeled oligonucleotides were purified on Whatman DE-52 DEAE-cellulose columns as described by R. B. Wallace, M. Schold, M. J. Johnson, P. Dembed and K. Itakura in 1981 in 9 Nucleic Acids Research 3647–3656. After filtration (0.2-$\mu$m-pore Nalgene filters), the probes were used directly for hybridization at a concentration of 0.2 ng/ml per species of probe (about $10^7$) total cpm.

Construction of recombinant plasmids. HCMV DNA was isolated according to the methods described by J. M. Demarchi in 1981 in 114 Virology 23–28 and by M. F. Stinski, E. S. Mocarski and D. R. Thompson in 1979 in 31 Journal of Virology 231–239. The viral DNA was released from purified virions by treatment with 2% sodium lauryl sarkosinate which was pretreated with 150 $\mu$q/ml proteinase K. After incubation at room temperature for thirty (30) minutes, the mixture was extracted with equal volumes of phenol and chloroform-isoamyl alcohol (24:1) by gentle shaking on a platform shaker. The DNA was precipitated from the aqueous layer with 95% ETOH.

Plasmid pBR327 was used as a cloning vector. The subgenomic fragments of HCMV DNA generated by digestion with restriction endonuclease Sau3A were ligated with BamHI cut plasmid pBR327 using T4 ligase. The recombinant plasmid was used to transform E. coli strain LSI, a lac[+] derivative of RRI (pro, leu, thi, rpsL20, hsdR, hsdM) by the procedure described by T. Maniatis, E. F. Fritsch and J. Sambrook in 1982 in Molecular Cloning: a Laboratory Manual (Cold Spring Harbor Laboratory, Cold Spring Harbor, N.Y.) at pages 254–255. Clones were selected on LB agar plate containing 20 $\mu$g/ml ampicillin.

Screening of HCMV library. Recombinant bacterial clones were screened on Whatman 541 filter papers, amplified with chloramphenicol (250 $\mu$g/ml) and prepared for hybridization as described by J. P. Gergen, R. H. Stern and P. C. Wensink in 1979 in 7 Nucleic Acids Research 2115–2136. The filters were prehybridized in 6× SET (1×SET=0.15 M Nacl/0.001 M EDTA/0.015 M Tris-HCl pH 7.5) containing 100 μg/ml sonicated salmon sperm DNA and 0.5% Nonidet P-40. Hybridization to the probe was performed at room temperature in the same buffer. Filters were washed first with 6× SSC (1×SSC=0.15 M Nacl, 0.015 M sodium citrate, pH 7.2) at room temperature. Three (3) high stringency washes were performed at 43° C. in the same buffer and then the filters were exposed to x-ray film.

Hybridization o f probes to plasmid DNA. Plasmid DNA was p repared according to an article published by D. Ish-Horowitz and J. D. Burke in 1981 in 9 Nucleic Acids Research 2989–2998. The $^{32}P$-labeled probes were hybridized to restriction enzyme-digested plasmid DNA on dried agarose gel at room temperature for approximately 16–18 hours. The buffer s used for hybridization and washes were the same as those used for colony hybridization.

Of the approximately 15,000 DNA fragments screened by hybridization to $^{32}P$-labelled HCMV probe 1, two (2) strongly hybridizing colonies were identified. When HCMV probe 2 was used for screening, positive hybridization was observed in the same two (2) colonies. The selection procedure included hybridization with probes at increasing temperatures in which the most stringent conditions approximated the predicted Td (dissociation temperature).

Plasmid DNA was prepared and inserts were analyzed by restriction enzyme mapping. The PstI digested recombinant plashwid DNA in the two (2) positive colonies was compared to PstI digested plasmid pBR327 DNA by electrophoresis on agarose gel. This comparison showed an insert of approximately 2.3 kb as the sequence of nucleotides in the DNA fragments in the two (2) positive colonies. When the recombinant plasmid DNA was digested with restriction enzyme Sau3A and compared with Sau3A digested plasmid pBR327 DNA, two additional fragments, a seven hundred twenty-one (721) bp and a fifteen hundred (1500) bp, were observed for both positive colonies. Of these two fragments, only the seven hundred twenty-one (721) bp fragment hybridized to the $^{32}P$-labeled synthetic probes on nitrocellulose filters by the Southern hybridization method (FIG. 3).

DNA sequence analysis. DNA restriction fragments were cloned into phage cloning vector M13 mp8 and single-stranded phage DNA was isolated as described by J. Messing and J. Vieira in an article published in 1982 in 19 Gene 269–276. Nucleotide sequence analysis was performed by a method using synthetic oligonucleotide primers. This method is described in an article published by F. Sanger, S. Nicklen and A.R. Coulsen in 1977 in 74 Proceedings of the National Academy of Science 5463–5467. Subfragments of the seven hundred twenty-one (721) bp insert were generated by using restriction endonucleases HpaII and SmaI and subjected to nucleotide sequence analysis after subcloning into bacteriophage M13 mp8 and mp9 respectively.

FIG. 2 shows the combined nucleotide sequence and the deduced amino acid sequences of the most relevant portion of the cloned insert. The tryptic mapping of the matrix protein of human cytomegalovirus (glycoprotein HCMVgp64) has been described in the article by Clark, Zaia, Balce-Directo and Ting specified above. Approximately 3 nanomoles of the HPLC purified matrix protein of human cytomegalovirus (HCMVgp64) were used for these studies and the recovery of tryptic peptides was greater than 90%. The HPLC purified tryptic peptides were arbitrarily numbered from T-1 to T-14 and subjected to amino acid composition analysis. On the basis of the amino acid composition, applicants selected two tryptic peptides T-12 and T-14 (both shown in FIG. 2) having respective retention times of 55.9 and 59.4 minutes, and applicants determined their amino acid sequences. These sequences were then compared with the amino acid sequences predicted from the nucleotide sequences of the cloned DNA. The predicted amino acid sequences were in total agreement with the sequences of the tryptic peptides T-12 and T-14 at the positions shown in FIG. 2.

In FIG. 2, the nucleotide sequences showing a perfect match with the probe sequence are underlined. Certain regions are indicated by bracketed lines. These are the regions where the predicted amino acid sequences are identical to the amino acid sequences of the two tryptic peptides. These are designated in FIG. 2, and discussed above, as T-12 and T-14.

Southern blot analysis. HCMV (Towne) DNA was digested to completion using restriction enzymes EcoRI, BamHI, HindIII and XbaI and by double digestion using BamlII and HindIII. The restriction digests were electrophoresed on agarose gels, stained with ethidium bromide, and blotted onto nitrocellulose. The cloned liCMV insert (721 bp) was nick translated with [α-$^{32}P$] dCTP (800 ci/m mol) using a nick translation kit (Amersham). Hybridization was conducted in a mixture containing 6× SSC, 1.0 mM EDTA, 5× Denhardt's solution, 0.5% sodium dodecyl sulfate and denatured salmon sperm DNA at 100, g/ml, at 68° for 16–18 hours. Filters were then washed with 0.1× SSC and 0.5% sodium dodecyl sulfate at 68° for 2 hours, dried and exposed to x-ray film a s discussed by EM. Southern in 1975 in 98 Journal of Molecular Biology 503–517.

Mapping of the gene coding for the matrix protein of human cytomegalovirus (HCMVgp64). The seven hundred twenty-one (721) bp HCMV insert was gel purified, nick translated and hybridized to HCMV DNA digested with restriction endonucleases EcoRI, BamHI, XbaI, HindIII and a digestion with both the restriction endonucleases BamHI and HindIII.

The restriction fragments were subjected to electropliore-sis on 0.7% agarose gels and visualized with an ethidium bromide stain. The results are shown in FIG. 3A. FIG. 3A shows the pattern of DNA fragments generated in the ethidium bromide-stained gel after digestion of HCMV DNA with EcoRI, BamHI, XbaI and HindIII. Columns 1, 2, 3 and 4 in FIG. 3A respectively s how the pattern of DNA fragments generated after digestion with the restriction endonucleases EcoRI, BamHI, HindIII and XbaI.

The DNA fragments were then transferred to nitrocellulose by Southern blotting and hybridized to $^{32}P$-labeled purified seven hundred twenty-one (721) bp cloned DNA. The filters were washed sequentially as follows: 1×SSC, 0.1% sodium dodecyl sulfate, for thirty (30) minutes at room temperature and 0.1×SSC, or 0.5% sodium dodecyl sulfate for two (2) hours at 68° C. After washing, the filters were subjected to autoradiography.

The HCMV restriction fragments showing hybridization to the labeled probe were characterized and are shown in FIG. 3B. Columns 1, 2, 3 and 4 in FIG. 3B respectively show the fragments hybridized to the labeled probe when the fragments were obtained by digestion of the cytomegalovirus DNA with the restriction endonucleases EcoRI, BamHI, HindIII and XbaI.

The HCMV restriction fragments showing hybridization to the labeled probe were characterized. These characterized fragments are shown in FIG. 3B. The slowest moving EcoRI fragment of HCMV in column 1 of FIG. 3B had a size of 23 kb in applicants' gels and hybridized strongly to the cloned fragment. In addition, strong hybridization was observed to a 6.15 kb BamHI fragment as shown in column 2 of FIG. 3B and to a large fragment (approximately 30 kb in size) of the HCMV-XbaI digest as shown in column 4 of FIG. 3B. The HCMV DNA digested with HindIII, and a BamHI/HindIII double digest (data not shown), gave a small fragment approximately 1 kb in size (as shown in column 3 of FIG. 3B) which showed hybridization to the same seven hundred twenty-one (721) bp probe.

Applicants have used the results of the Southern blots, shown in FIG. 3 and discussed in the previous section, to locate the cloned gene fragment coding for the matrix protein, such as HCMVgp64, on the HCMV genome. FIG. 4 illustrates the restriction endonuclease maps for the Towne strain of HCMV. Each of the first four (4) rows of FIG. 4 shows the location for the different DNA fragments when the cytomegalovirus DNA are respectively digested by the restriction endonucleases XbaI, HindIII, BamHI and EcoRI. The last row of FIG. 4 shows mapping units between 0.0 and 1.0 and identifies the location in such mapping units of each of the DNA fragments in the first four rows of FIG. 4.

The different letters in each row in FIG. 4 identify the location of the different DNA fragments in that row. The map locations of the DNA fragment hybridized to the probe after digestion of the cytomegalovirus DNA fragment of seven hundred twenty-one base p airs (721 bp) with the different restriction endonucleases are indicated at A in the fourth row (IICMV EcoRI), at P in the third row (HCMV-BamHI) and at C in the first row HCMV-XbaI) and are shown by bracketed underlines in such rows. More precisely, the map location has been assigned a position between fragments Hi and N in the second row in FIG. 4. This position is indicated by an arrow in the second row (HCMV-HindIII) of FIG. 4.

Experiments with cloned DNA a. Detection of viral sequences in HCMV infected cells by dot-blot hybridization FIG. 5 specifies the nucleotide sequence of a $^{32}P$-labelled nick translated 721 bp Sau3A fragment of the recombinant plasmid. This DNA fragment contains the exact nucleotide sequences as predicted from the amino acid sequence of tryptic peptide of HCMVgp64. This DNA fragment was used as a hybridization pro b e to analyze by dot-blot analysis the purified DNAs or cell lysates from human foreskin fibroblast cell lines infected with three different HCMV lab strain s (Towne, Ad 169 and Davis). In a similar experiment this probe was used to analyze other herpes viruses (FIG. 6), which included two (2) strains of simian CMV (Rhesus and Verret), two (2) strains of VZV (212B and target), two (2) strains of ISV-1 (McIntyre and BK) and two strains of HSV-2 (MS and 186). DNA from uninfected cells was used as negative controls. In this experiment, the labelled cloned 740 bp fragment hybridized specifically only to the DNA of HCMV and showed no hybridization to the DNA from other herpes viruses (FIG. 6). These results indicate that the cloned DNA fragment is specific for HCMV and can be used as a specific probe for detecting HCMV sequences during HCMV infection.

In a similar experiment, the $^{32}P$-labelled 740 bp cloned fragment was also used for analyzing a number of wild isolates of HCMV. Five (5) different wild isolates including three (3) isolates from granulocyte cultures from patients after bone marrow transplantation, one lung tissue isolate from a patient with HCMV associated pneumonia and one isolate from granulocytes of a patient with acquired immunodeficiency syndrome (AIDS) were used. Purified DNA from HICMV (Towne) were used as a positive control and DNA from uninfected cells were used as negative control. Using this technique, all of the five (5) clinical isolates were found to be expressing HCMV DNA (FIG. 7).

b. Identification of UICMV-infected cells by in situ-cytohybridization

This technique provides a means of identifying specific cells which are expressing a specific gene. In general, only those cells actively expressing the gene in question will contain enough copies of homologous RNA to hybridize with the radioactively-labelled probe sufficiently to produce a signal detectable by autoradiography. CDV-infected cells were deposited on oxides, fixed, treated with HCE followed by heating at seventy degrees (70° C.), digested with proteinase K, and dehydrated in graded ethanol. DNA-RNA in situ cytohybridization was conducted overnight at twenty to thirty degrees (20°–30°) C. The slides were washed extensively in hybridization buffer and dehydrated in graded ethanol and DNA-RNA hybrids were detected. Using this technique, $^{32}P$-labelled nick translated recombinant plasmid containing the nucleotide sequences coding for HCMVgp64 was able to distinguish, from the uninfected cells, human cell lines which were infected with HCMV.

Discussion

As discussed by M. F. Stinski in 1977 in 23 Journal of Virology 751–767 and by M. W. Wathen and M. F. Stinski in 1982 in 41 Journal of Virology 462–477, HCMV has been shown to undergo regulated phases of transcription a nd translation, thus giving rise to immediate-early, early and late transcripts. While some of the immediate early (IE) viral proteins may have regulatory functions necessary for efficient transcription, the late transcripts comprise largely the structural polypeptides. Several groups have reported the cloning of restriction fragments of HCMV in plasmid and cosmid vectors. This has provided a basis for constructing cleavage maps and determining the structural organization of the HCMV genome. Furthermore, the transcription pattern of HCMV genome has been investigated at various phases of infection as reported by J. M. Demarchi in 1981 in 114 Virology 23–38 and M. W. Wathen and M. F. Stinski in 1982 in 41 Journal of Virology 462–477.

In order to correlate a defined virion protein with the respective coding sequence, applicants have utilized an approach which is based on protein sequence information. Synthetic oligonucleotides modeled after the amino acid sequences of the matrix protein of human cytomegalovirus, such as HCMVgp64, were utilized for the probing of a library of HCMV subgenomic DNA. Recent advances in protein purification and microsequencing have made this approach quite general, relatively rapid and applicable to many viral proteins.

The use of relatively short probes up to 14 bases has long been known to give frequent false positives in which the clones have only partial nucleotide matches with the probes. The use of either two overlapping probes or a second probe directed against a different site in the protein has been suggested to overcome this problem. Applicants evaluated two oligonucleotide probes seventeen (17) bases and twenty (20) bases in length because applicants were not certain what length (and sequence complexity due to codon degeneracy) would be necessary for optimal screening efficiency. Applicants' results have demonstrated that a mixture of sixteen (16) heptadecanucleotides and a mixture of thirty-two (32) eicosanucleotides are similar in terms of giving strong signal-to-noise ratio in both colony screening and plasmid DNA screening.

By comparing nucleotide sequences with amino acid sequences of tryptic peptides, evidence has been provided that the cloned DNA contains sequences coding for the matrix protein of human cytomegalovirus such as HCMVgp64. The strategy that applicants used to obtain such information is as follows:

Applicants determined amino acid compositions of all the purified tryptic peptides produced from the matrix protein of human cytomegalovirus such as HCMVgp64. Of these peptides, applicants initially selected the sequence T-14 (see FIG. 2) for microsequencing. Analysis of the amino acid sequence of this peptide provided a single sequence through the COOH-terminus and provided information for the design of synthetic probes. The entire amino acid sequence of this peptide was later revealed to have complete agreement with the nucleotide sequence of a portion of the cloned DNA, thus providing evidence that the cloned DNA coded for the matrix protein of human cytomegalovirus such as HCMVgp64.

To further confirm this identity between the amino acid sequence of the peptide and the nucleotide sequence of a portion of the cloned DNA, applicants identified another tryptic peptide T-12 (see FIG. 2), which, on the basis of amino acid composition, corresponded to a region located 3' to the coding sequences of T-14. When subjected to microsequence analysis, this peptide also yielded a unique sequence and showed a perfect match with the amino acid sequence deduced from the nucleotide sequence. Applicants believe that these results provide the first information of the amino acid and gene sequences of the matrix protein of human cytomegalovirus such as HCMVgp64.

Very little has been known in terms of precise map positions of the genes encoding specific HCMV proteins. Stinksi et al have recently identified, in an article published by them in 1983 in 46 Journal of Virology 1–14, the coding region of a 72K dalton immediate-early protein by in vitro translation of mapped mRNA. However, the mapping of the structural proteins of HCMV has not been reported to date. In herpes simplex virus, the use of intertypic recombinants based on its mutants has permitted the physical mapping of a number of structural polypeptides. This has been disclosed by H. S. Marsden et al in 1978 in 28 Journal of Virology 624–642 and by L. S. Morse et al in 1978 in 26 Journal of Virology 389–410. However, in the case of a slowly replicating virus such as HCMV, such an approach has not been feasible.

The method for mapping disclosed and claimed in this application utilizes a cloned DNA which contains the nucleotide sequences coding for a defined virion polypeptide. This method is accordingly a relatively direct route to the mapping of specific proteins. Using this approach, applicants have been able to characterize and physically map the coding sequences of the matrix protein of human cytomegalovirus, such as HCMVgp64, in an area of HCMV genome which has been observed not to be homologous to cellular genes.

It has been previously shown by Clark et al in 1984 in 49 Journal of Virology 279–282 that the matrix protein of human cytomegalovirus such as HCMVgp64 contains approximately 2.34% (wt/wt) of galactosamine. The exact function of this protein and a uniform nomenclature have not been established. However, HCMVgp64 appears to be a matrix protein based upon parallel studies with the Colburn strain CMV, a simian virus. This protein is overproduced late in infection, and it forms more than ninety percent (90%) of the protein mass of HCMV dense bodies, which are membrane-bound, DNA-free, protein aggregates. The antigens conventionally used for HCMV serologic testing are rich in the matrix protein of human cytomegalovirus, such as HCMVgp64, and antibody to this protein occurs after natural infection. The role of the matrix protein of human cytomegalovirus, such as HCMVgp64, during natural infection is not known, but it is possible that, if overproduction of this material occurs in vivo, it will have some influence on pathogenesis of HCMV disease.

The cloning of the gene for the matrix protein of human cytomegalovirus, such as HCMVgp64, should make it possible to produce, by chemical synthesis or by expression in prokaryotic or eukaryotic cells, polypeptides containing this sequence and variations of this sequence. The expressed proteins should provide material that will be useful as a laboratory diagnostic reagent.

This has been confirmed by tests which have been performed with a cloned 800 base pair DNA fragment obtained as discussed above. This DNA fragment codes for a portion of the matrix protein of the human cytomegalovirus, such as the 64K dalton glycoprotein. This DNA fragment has been used as a probe for HCMV-specific DNA sequences infection cells. This portion of the genome has not been reported to be homologous to either cellular or onc genes. The eight hundred base pair (800 bp) DNA was $^{32}P$-labeled.

Applicants have used the labeled DNA fragment as a probe in dot blot assays to determine whether the cloned fragment would hybridize to various herpes virus-infected cells and uninfected cells. These herpes virus-infected cells included cells infected with three laboratory strains of human cytomegalovirus (Towne, AD169 and Davis) and with all clinical isolates of human cytomegalovirus. The herpes virus cells also included herpes simplex virus types 1 and 2, varicella, zoster virus and several simian cytomegaloviruses.

In the tests specified in the previous paragraph, hybridization was detected with extracts from cells infected with the three laboratory strains of HICMV (Towne, AD169 and Davis) and with all clinical isolates tested to date. The cloned fragments did not hybridize to extracts from cells infected with herpes simplex virus types 1 and 2, varicella zoster virus, the different simian cytomegalovirus and the uninfected cells. Since the fragment coding for the matrix protein of human cytomegalovirus, such as HCMVgp64, appears to hybridize specifically only with nucleotide sequences found in HCMV-infected cells, this probe can be used to differentiate HCMV from other herpes viruses.

The tests performed to diagnose human cytomegalovirus (HCMV) have advanced through several stages. Initially the effectiveness of the in situ cytohybridization technique was demonstrated on human foreskin fibroblast cells maintained in culture and infected with HCMV in vitro. The results demonstrated the specificity of the probe of the matrix protein of human cytomegalovirus, such as HCMVgp64, to such in vitro infected cells and the lack of specificity of such matrix protein probe to uninfected control cells. Subsequently this technique was shown to be effective on sections of lung tissue taken at autopsy from bone marrow transplant patients who had died from HCMV pneumonia. In other words, the probe hybridized specifically to HCMV-infected lungs.

Applicants have determined that there is a T-lymphocyte reactivity to the matrix protein of human cytomegalovirus (HCMVgp64) following natural infection of an individual with HCMV. This is the first HCMV protein to which T-lymphocyte reactivity has been demonstrated. Because T-lymphocyte immunity appears to be important for recovery from HCMV infection, HCMVgp64 appears to be a candidate vaccine for HCMV.

To confirm the discussions in the previous paragraph, peripheral blood mononuclear leukocytes were separated using Ficoll-hypaque, washed, suspended in RPMI-1640 medium with ten percent (10%) AB+, Rh+ human serum and were then cultured at 37° C. in microtiter plates ($10^5$ cells/well). Different samples of the peripheral blood mononuclear leukocytes were then stimulated with optimal dilutions of individual ones of (a) the matrix protein of human cytomegalovirus (HCMVgp64) such as HCMVgp64, (b) HCMV-infected cell lysate and (c) control cell lysate, and cultures were analyzed for proliferation and for lymphokine production.

The matrix protein of human cytomegalovirus (4 μg/ml) stimulated $H^3$-thymidine in HCMV seropositive donor peripheral blood mononuclear leukocytes but not in seronegative donor peripheral blood mononuclear leukocytes. The peripheral blood mononuclear leukocytes produced the same stimulation with HCMV-infected cell lysate as when the matrix protein of human cytomegalovirus (HCMVgp64) was used. The matrix protein of human cytomegalovirus (HCMVgp64) induced interleukin-2 (IL-2) production, IL-2 receptor expression and interferon production. The addition of antibody to the IL-2 receptor blocked the reactivity of the peripheral blood mononuclear leukocytes to HCMVgp64.

Polynucleotide HCMV Vaccine

As explained, this invention relates to methods of using DNA fragments coding for a major late 64 kilodalton protein, also known as pp65, of human cytomegalovirus (HCMVgp64) to prevent the disease. Pursuant to this aspect of the invention, pp65 has been shown to be a major CTL target during natural infection and hence useful as a component of a HCMV polynucleotide vaccine. The invention accordingly includes pp65 expression vectors under the control of various promoters including, but not limited to, human β actin promoter and HCMV immediate early promoter preferably along with the intron A (HCMV-IE/intron A). These DNA constructs may be administered by intramuscular injection or in any other way known or within the skill of the art.

Background—HCMV Polynucleotide Vaccine

Human cytomegalovirus (HCMV) is an opportunistic pathogen which is capable of causing disease that affects all age groups. Although primary infection in the immunocompetent host is often asymptomatic, a state of life-long latency is established. However, severe immunosuppression can cause reactivation of the HCMV infection from the latent state with the potential to cause severe and widespread disease in the immunocompromised host (Alford, C. A., et al., "In Virology" (B. N. Fields, D. M. Knipe et al. Eds.) Second Ed., Raven Press, New York (1990)).

Protective immune responses against HCMV are as yet incompletely defined, although numerous immune effector functions have been described following HCMV infection (Quinnan, G. V., et al., N.Engl.J.Med. (1982) 307:7–13; Reusser, P., et al., Blood (1991) 78:1373–1380). In an effort to analyze virus-encoded targets that are responsible for these responses, it has become clear that a number of HCMV-specific polypeptides, including the envelope glycoproteins and the internal proteins of the virus, are significant targets of immune resolution (Borysiewicz, I. K., et al., J.Exp.Med. (1988) 168:191–931; Liu, Y- N.C., et al. J.Virol. (1988) 62:1066–1070; Forman, S. J., et. al., J. Immunol. (1985) 134:3391–3395). The ideal target antigen(s) needed to elicit a protective immune response would be one that is abundant, highly conserved, presented early in the HCMV-infected cell, capable of eliciting humoral, and more importantly, cell-mediated immune responses, and not susceptible to virus-induced mechanisms that limit antigen presentation. Applicants have previously shown that the HCMV tegument protein pp65, one of the most abundant constituents of the HCMV virion, is highly conserved in HCMV strains (Pande, H., et al., Virology (1991) 182:220–228). The protein can stimulate significant immunologic activity in a manner similar to that of the whole virus, including lymphoproliferation, IL-2 and interferon production, B-cell stimulation of antibody, and natural killer activity (Forman, supra). This polypeptide has also been shown to induce humoral immune response, although the antibody response to this protein appears to be variable in HCMV-infected individuals (Pande, supra; Zaia, J. A., et al., Infect. Dis. (1986) 153:780–787; Plachter, B., et al., J. Clin.Microbiol. (1990) 28:1229–1235). More recently, applicants have shown that this protein serves as a significant target of a CD8+, class I major histocompatibility complex (MHC)-restricted, HCMV-specific cytotoxic T-lymphocyte (CTL) response in all seropositive individuals studied (McLaughlin-Taylor, E., et al., J.Med.Virol. (1994) 43:103–110). These immunological properties of pp65, make it an ideal candidate to be considered as a component of a HCMV vaccine.

Conventional vaccines utilize either live infectious material or inactivated protein/subunit preparations for introducing antigenic material suitable for inducing protective immunogenic responses. Live vaccines can mimic natural infection and generate humoral and cellular reactivity (Plotkin, Science (1994) 265:1383–1385). However, subunit vaccines comprised of soluble proteins are not necessarily taken up by antigen-presenting cells and are not efficiently processed by the class I antigen processing pathway. Thus, cellular immune reactivity will not be complete using protein-based vaccines until an appropriate adjuvant is developed which increases the efficiency of this cellular uptake and processing (Raychaudhuri, S., et al., Immunol. Today (1993) 14:344–348).

Polynucleotide vaccines (DNA-based vaccines), involving the use of antigen-expressing DNAs for vaccination, represent a new concept for immunization. This approach results in the in vivo synthesis of the encoded antigen in the host cells (Wolff, J. A., et al., Science (1990) 247:1465–1468). The de novo synthesized protein is accessible to normal cellular processing and modifications, thus having the possibility of induction of humoral as well as cell mediated immune responses including the generation of protective cytotoxic T-lymphocytes (CTLs) that recognize antigenic peptides in association with the MHC class I molecules (Tang, D. -C., et al., Nature (1992) 356:152–154; Ulmer, J. B., et al., Science (1993) 259:1745–1749). In addition to conceptually mimicking some aspects of attenuated vaccines, one of the major advantages of this approach is the avoidance of the inherent risks associated with infectious agents or virus particles.

DESCRIPTION OF FIGS. 8, 9, AND 10

Figure 8:
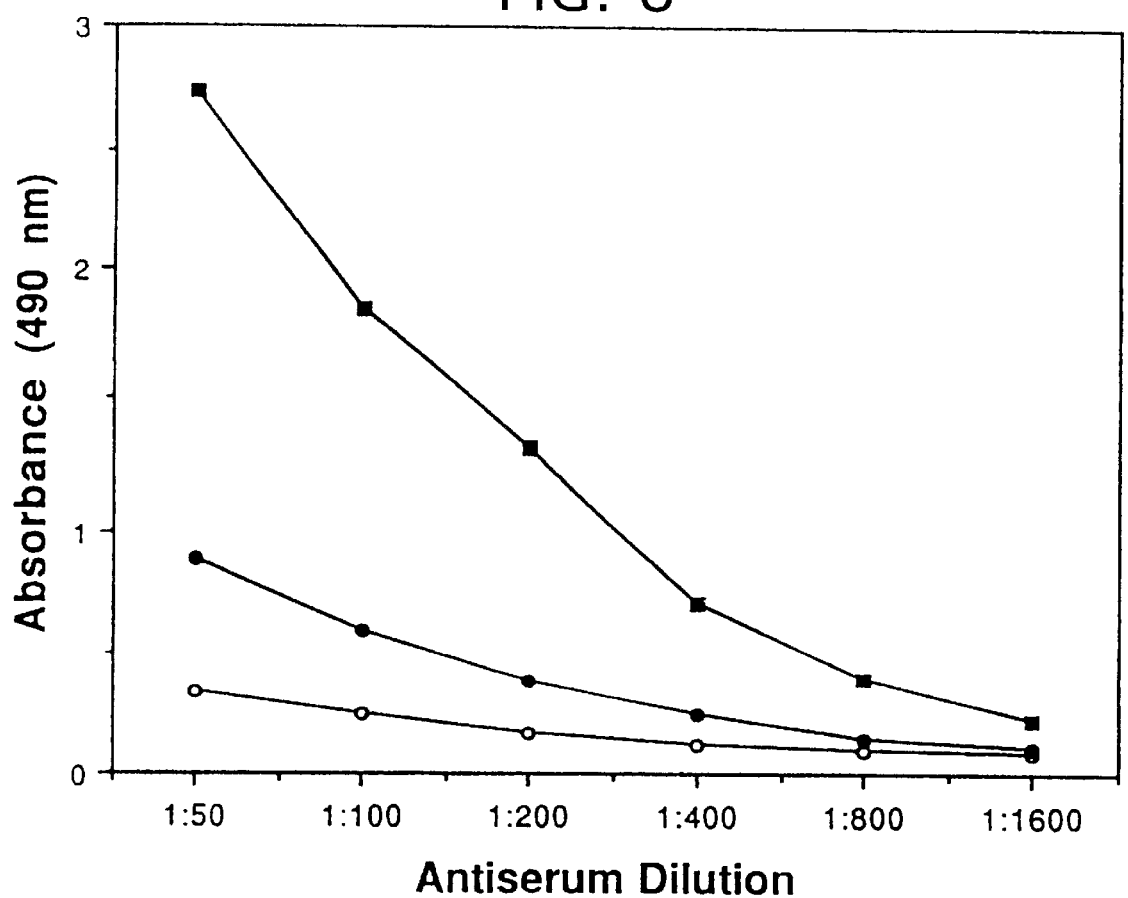

FIG. 8 illustrates antibody response to the HCMV tegument protein pp65 generated after intra-muscular injection of pCMVint-pp65 DNA in BALB/c mice. IgG anti-pp65 antibodies were measured by ELISA using the virion-purified pp65 as the solid-phase antigen. Serum samples were serially diluted starting at 1:50 and used in a standard ELISA as described in the text. Antisera tested were from preimmune mice (-O-); from a mouse producing high-titer anti-pp65 (-■-); and the average from a group of 5 mice (-●-).

Figure 9:
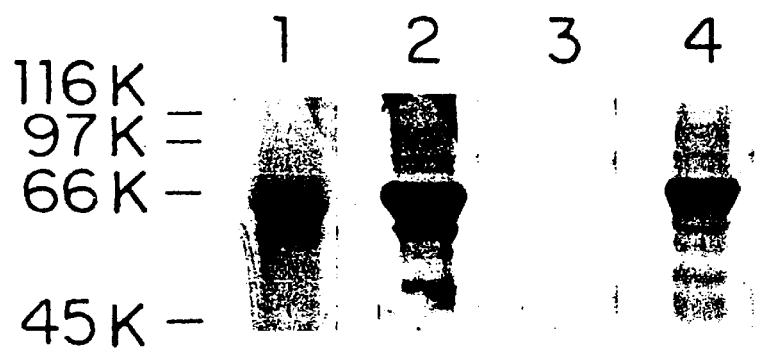

FIG. 9 illustrations detection of anti-pp65 antibodies in the sera of genetically immunized mice by Western blot analysis. The virion-purified pp65 was electrophoresed on a 10% SDS-PAGE and either stained with Coomassie blue to visualize the protein band (lane 1); or electrophoretically transferred to nitrocellulose membrane and analyzed by immunoblot analysis using a positive control monoclonal antibody, 28-103, used at a 1:750 dilution (lane 2), a preimmune serum collected from the mouse prior to DNA injection and used at a 1:100 dilution (lane 30, and a serum sample from a genetically immunized animal collected at four weeks post-boosting and used at a 1:100 dilution.

Figure 10:
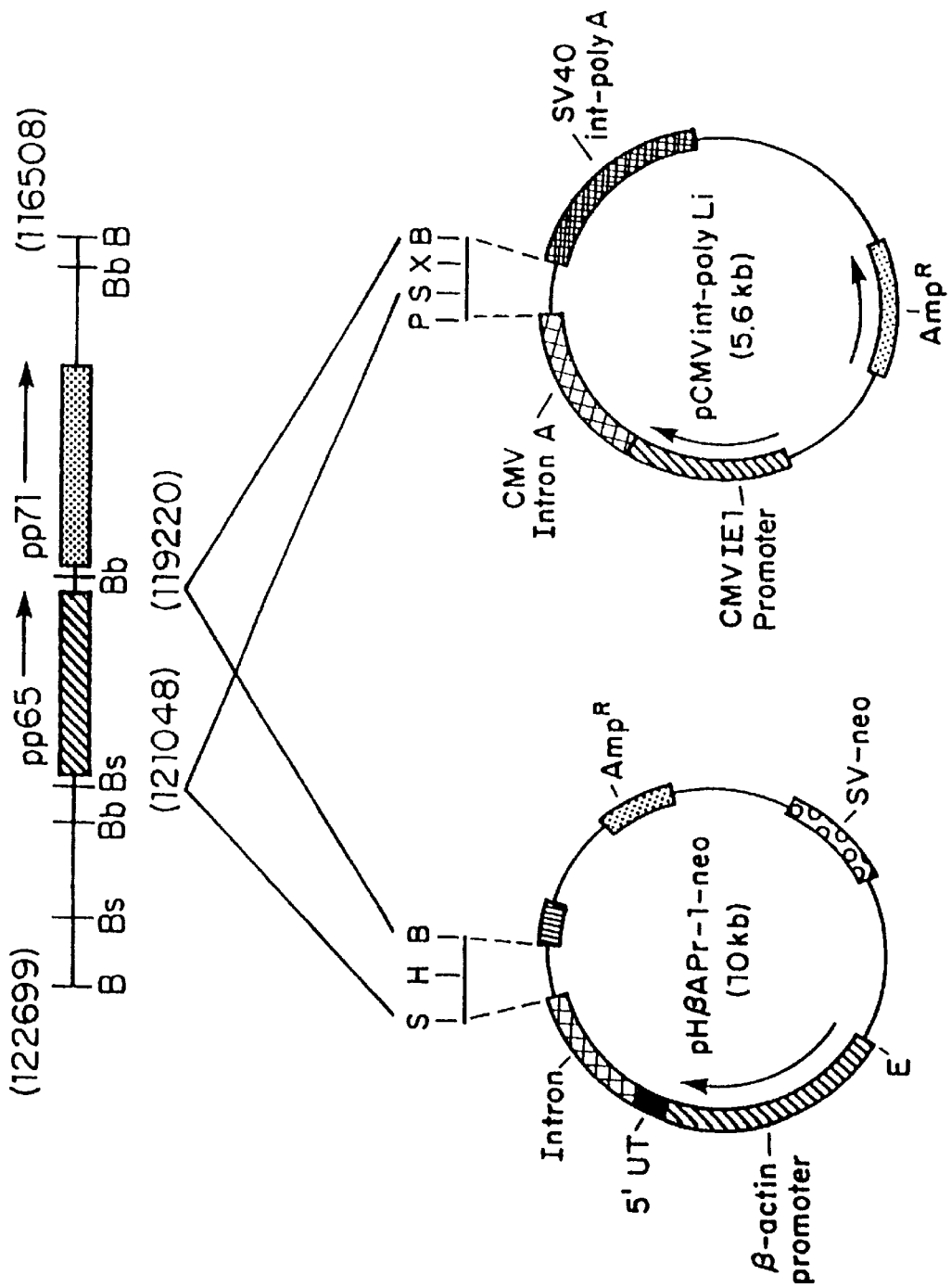

FIG. 10 depicts two plasmid constructs including Phβ-pp65.

General Description of The Polynucleotide HCMV Vaccine

Applicants have utilized plasmid vectors expressing the tegument protein pp65 for the direct DNA immunization in mice, and examined the feasibility of this approach to generate antibody response to the encoded protein. Two plasmids were constructed including Phβ-pp65, in which pp65 expression is driven by the human β-actin promoter (Gunning, P., et al., *Proc.Natl.Acad.Sci.* (1987) 84:4831–4836), and pCMVint-pp65, in which pp65 expression is under the control of HCMV immediate early promotor and intron A (HCMV-IE/intron A) (Manthorpe, M., et al., *Hum.Gene Ther*. (1993) 4:419–431), and compared for their ability to generate pp65 specific antibodies.

Materials and Methods

Construction of pp65 expression plasmids:

The plasmids pHβ-pp65 and pCMVint-pp65 (see FIG. 10) were constructed by inserting a 1828 bp fragment corresponding to nucleotides 119,220 to 121,048 of HCMV DNA (Chee, M. S., et al., *Curr.Top.Microbiol.Immunol.* (1990) 154:125–169), containing the entire coding sequence for pp65 between the unique SalI and BamHI restriction sites in the plasmid vectors pHβAPr-1-neo (Gunning, supra) and pCMVint-polyLi respectively (Manthorpe,M., supra).

In vivo gene transfer:

BALB/c mice (4 to 5 weeks of age) were obtained from Jackson lab (Bar Harbor, Maine) and a week later were injected in the quadriceps muscle of one leg with either pHβ-pp65 or pCMVint-pp65 plasmid DNA using the method described by Wolff et al., supra. Briefly, the mice were anaesthetized using Metophane (methoxyflurane), a small incision (~1 cm) was then made in the skin over the quadriceps to clearly visualize the underlying muscle, and the plasmid DNA was injected directly into the muscle using a 28 gauge needle and a 0.5 ml insulin syringe. A William's collar consisting of teflon tubing was used with the needle to insure that the final injection depth was no more than 0.2 cm. The mice were injected with a solution containing 100 µg of plasmid DNA in 50 µl of sterile saline and the skin was subsequently closed using silk sutures. A booster injection consisting of 100 µg plasmid DNA in 50 µl sterile saline was administered five weeks later. Blood was withdrawn from the orbital sinus at two and four weeks after the initial immunization and at four weeks after the booster.

Detection of specific antibodies by ELISA and immunoblot analysis:

To evaluate antibody response in mice after immunization with the plasmid DNA, applicants initially used a standard enzyme-linked immunosorbant assay (ELISA). ELISAs were run in 96-well EIA plates (Costar, Cambridge, Mass.) that had been coated overnight at 4° C. with 50 µl of a solution containing 8 gg/ml of pp65, purified form isolated virions as previously described (Clark, B. R., et al., *J. Virol.* (1984) 49:279–282) and diluted in a carbonate buffer. Plates were then incubated with a blocking buffer (PBS with 1% BSA and 0.3% gelatin) for one hour at 23° C., followed by the sample consisting of a serial dilution of mouse serum for two hours, a secondary antibody conjugated to horseradish peroxidase, and finally the substrate O-phenylene diamine. The reaction was stopped with 2N $H_2SO_4$, and the plates were read at 490 nm using an EIA reader (MR600, Dynatech).

For the immunoblot analysis the virion-purified pp65 was subjected to SDS-polyacrylamide gel electrophoresis (SDS-PAGE) using a 10% gel, followed by electrotransfer onto a nitrocellulose membrane. The individual stips were analyzed by immunoblot analysis using a positive control monoclonal antibody, 28-103, a preimmune serum collected from the mouse prior to DNA injection, and a serum sample from a genetically immunized animal collected at four weeks post-boosting. Staining was done using a biotinylated second antibody and the ABC kit (Vector Laboratories), with 4-chloro-1-naphthol as substrate.

Anti-pp65 titers assayed in the serum collected after two and four weeks of initial immunization appeared rather low (data not shown). However, using the sera collected four weeks after the boost, a number of mice showed the presence of pp65-specific antibodies, while the preimmune sera or the sera from uninjected mice contained no detectable anti-pp65 antibody (FIG. 8). Applicants compared the antibody titers in the two groups of mice that received either pHβ-pp65 or pCMVint-pp65 plasmid DNA injections by defining high-titer as >1 absorbance units in 1:50 serum dilution, and low-titer as <1 absorbance unit in 1:50 serum dilution. In the group of mice that were injected with pCMVint-pp65 DNA, approximately 20% of the mice contained high-titer anti-pp65 antibody, 40% of the mice showed the presence of low-titer anti-pp65 antibody, and 40% of the mice had no detectable anti-pp65 antibody. In the mice that received pHβ-pp65 DNA injections, approximately the same number of mice as the first group showed the presence of pp65-specific antibodies. However, in this group, applicants did not detect any mice with high-titer anti-pp65 antibody, whereas, approximately 60% of the mice had low-titer anti-pp65 antibody, and 40% of the mice had no detectable anti-pp65 antibodies.

Additional proof for the generation of pp65-specific antibodies in mice as a result of DNA immunization came from the immunoblot analysis of the murine serum obtained at four weeks after the boost (FIG. 9). Virion-purified pp65 was immobilized on a nitrocellulose filter by electrophoresis using SDS-PAGE, followed by electrotransfer. The individual strips were sliced and treated with either a pp65-specific monoclonal antibody or the test mouse sera. In this assay, a 1:100 dilution of the test sera reacted very strongly with the purified pp65 (FIG. 9, lane 4), as did a 1:750 dilution of a monoclonal antibody 28-103 (FIG. 9, lane 2), which is specific for pp65, whereas the prebleed from the same mouse obtained prior to DNA injections showed no reactivity to pp65 (FIG. 9, lane 3).

In summary, applicants have shown that a DNA-based immunization of mice with plasmid DNAs encoding the tegument protein pp65 resulted in the generation of pp65-specific antibodies. Approximately 60% of the mice showed the presence of anti-pp65 antibodies following the second DNA inoculation with plasmid DNA. The anti-pp65 antibody titer was higher in the group of mice that was injected with pCMVint-pp65 DNA compared to the group that was injected with pHβ-pp65 DNA. Plasmids containing the HCMV-IE/intron A have been shown to be superior to plasmids containing the human β-actin promoter for the in vivo expression of the encoded protein (Chee, supra).

However, this is the first report that shows that the DNA immunization using a plasmid containing the HCMV-IE/intron A results in the generation of higher antibody titers compared to a plasmid where the expression of the encoded gene is driven by the human β-actin promoter.

Live HCMV vaccines based on intact proteins or specific peptides are attended by production and adjuvant-related problems. Virus vectors involve safety and quality control problems. The HCMV specific DNA or polynucleotide vaccines of this invention are free of these problems.

What is claimed is:

1. An isolated nucleotide sequence which comprises (SEQ ID NO:6).

2. A method of immunizing a human patient having human cytomegalovirus comprising:
(a) providing HCMVpp65 protein; and (b) administering the HCMVpp65 protein to the human patient to obtain a reaction with the patient's T-lymphocytes.

3. An immunogenic composition for human cytomegalovirus (HCMV) in which the immunogen is an HCMV antigen, said HCMV antigen comprising the 64 kilodalton glycoprotein HCMVgp64 purified from the virions plus dense bodies, said purified glycoprotein HCMVgp64 being characterized by stimulated $H^3$-thymidine in HCMV seropositive donor peripheral blood mononuclear leukocytes but not in seronegative peripheral blood mononuclear leukocytes.

4. An immunogenic composition for increasing the immune response to cytomegalovirus in a human patient comprising a DNA fragment coding for the late major 64 kilodalton protein (pp65) of human cytomegalovirus.

5. A DNA construct comprising a vector that expresses human cytomegalovirus pp65.

6. An immunogenic composition for increasing the immune response to cytomegalovirus in a human patient comprising a fragment having nucleotides 119,220 to 121,048 of HCMV DNA.

7. An immunogenic composition for increasing the immune response to cytomegalovirus in a human patient, the vaccine comprising HCMVpp65 protein.

8. An immunogenic composition for human cytomegalovirus (HCMV) in which the immunogen is an HCMV antigen, said HCMV antigen comprising an isolated 64 kilodalton glycoprotein HCMVgp64, said glycoprotein being capable of inducing interleukin-2 (IL-2) production, IL-2 receptor expression, and interferon production in peripheral blood mononuclear leukocytes.

* * * * *

UNITED STATES PATENT AND TRADEMARK OFFICE
CERTIFICATE OF CORRECTION

PATENT NO. : 6,133,433
DATED : October 17, 2000
INVENTOR(S) : Pande et al.

It is certified that error appears in the above-identified patent and that said Letters Patent is hereby corrected as shown below:

Title page,
Item [57], ABSTRACT,
Line 10, insert -- The probe may be radioactively labelled, and can screen DNA fragments constituting a subgenomic library of human cytomegalovirus DNA to obtain DNA fragments coding for the major late protein of human cytomegalovirus. --

Signed and Sealed this

Seventeenth Day of August, 2004

JON W. DUDAS
*Acting Director of the United States Patent and Trademark Office*